United States Patent [19]

Casci et al.

[11] Patent Number: 4,528,171
[45] Date of Patent: Jul. 9, 1985

[54] ZEOLITE AND PROCESS FOR PREPARING THE SAME

[75] Inventors: John L. Casci, Redcar, England; Barrie M. Lowe, Edinburgh, Scotland; Thomas V. Whittam, Darlington, England

[73] Assignee: Imperial Chemical Industries, PLC, England

[21] Appl. No.: 367,615

[22] Filed: Apr. 12, 1982

[30] Foreign Application Priority Data

Apr. 14, 1981 [GB] United Kingdom ............... 8111851

[51] Int. Cl.$^3$ .............................................. C01B 35/10
[52] U.S. Cl. .................................... 423/277; 423/326; 423/328; 423/329; 423/330; 423/332; 423/333; 502/61; 502/62; 502/64; 502/77; 502/202
[58] Field of Search ................................ 423/326-333; 252/455 Z; 502/77, 202, 62

[56] References Cited

U.S. PATENT DOCUMENTS

| | | | |
|---|---|---|---|
| 3,700,585 | 10/1972 | Chen et al. | 423/328 |
| 3,832,449 | 8/1974 | Rosinski et al. | 423/328 |
| 3,947,482 | 3/1976 | Albers et al. | 423/329 |
| 4,116,813 | 9/1978 | Rubin et al. | 252/455 Z |
| 4,208,305 | 6/1980 | Kouwenhoven et al. | 423/328 |
| 4,268,420 | 5/1981 | Klotz | 423/326 |
| 4,299,808 | 11/1981 | Klotz | 423/326 |

Primary Examiner—Gary P. Straub
Assistant Examiner—Jackson Leeds
Attorney, Agent, or Firm—Cushman, Darby & Cushman

[57] ABSTRACT

A synthetic zeolite material, designated zeolite EU-4, having a molar composition expressed by the formula:

$$0 \text{ to } M_2O : aY_2O_3 : \text{at least } 100\ XO_2 : 0 \text{ to } 35\ H_2O$$

wherein M is a monovalent cation or 1/n of a cation of valency n, a is from 0 to 9, X is silicon and/or germanium, Y is one or more of aluminum, iron, chromium, vanadium, molybdenum, arsenic, antimony, manganese, gallium or boron, and $H_2O$ is water of hydration additional to water notionally present when M is H, and having a defined X-ray diffraction pattern is prepared from an aqueous reaction mixture containing the oxide $XO_2$, optionally the oxide $Y_2O_3$ and an alkyltrimethylammonium or dialkyldimethylammonium compound.

Zeolite EU-4 is a useful catalyst for methanol conversion and the like.

8 Claims, No Drawings

ZEOLITE AND PROCESS FOR PREPARING THE SAME

The present invention relates to a zeolite material, hereinafter referred to as zeolite EU-4, to a method of making it and to processes using it as a catalyst.

According to the present invention we provide zeolite EU-4 having a molar composition expressed by the formula:

0 to $9M_2O : aY_2O_3$ : at least $100\ XO_2 : 0$ to $35H_2O$ wherein M is a monovalent cation or $1/n$ of a cation of valency n, a is from 0 to 9, X is silicon and/or germanium, Y is one or more of aluminium, iron, chromium, vanadium, molybdenum, arsenic, antimony, manganese, gallium or boron, and $H_2O$ is water of hydration additional to water notionally present when M is H, and having an X-ray pattern substantially as set out in Table 1 (as determined by standard technique using copper Kα radiation). Table 1 shows X-ray data for zeolite EU-4 as prepared. Only the most significant spacings are given. The X-ray pattern is little affected by the type of cation present.

state of high purity when the number of moles of $Y_2O_3$ is in the range 0 to 2.5.

This definition includes both freshly prepared zeolite EU-4 ("freshly prepared" means the product of synthesis and washing, with optional drying, as hereinafter described) and also forms of it resulting from dehydration, and/or calcination, and/or ion exchange. In freshly prepared zeolite EU-4, M may include an alkali metal cation; especially sodium, and/or ammonium, and usually or when prepared from alkylated nitrogen compounds, includes nitrogen-containing organic cations as described below or cationic degradation products thereof, or precursors thereof. These nitrogen containing cations are hereinafter referred to as Q.

The freshly prepared zeolite EU-4 may also contain nitrogen-containing compounds well in excess of the 18 moles set out in the aforesaid definition of the composition of zeolites EU-4, typically in the range 1 to 40 moles per mole of $Y_2O_3$. Since EU-4 is a zeolite, the excess nitrogen-containing base must be physically trapped within the crystal lattice, because it is too large to escape. It can only be removed by thermal or oxidative degradation. This physically trapped basic material does not constitute part of the composition for the purposes of the definition. Thus a zeolite EU-4 as made typically has the following molar composition:

0 to $9M_2O : 1$ to $40\ Q^+ : Y_2O_3 : 100\ XO_2 : 0$ to $35H_2O$ wherein M is an alkali metal or ammonium.

The $H_2O$ content of freshly prepared or hydrogen zeolite EU-4 depends on the conditions in which it has been dried after synthesis.

In calcined forms of zeolite EU-4, M may be alkali metal but includes less or no nitrogen-containing organic compounds, since these are burnt out in the presence of air, leaving hydrogen as the other balancing cation.

Among the ion-exchanged forms of zeolite EU-4 the ammonium ($NH_4^+$) is of importance since it can be readily converted to the hydrogen form by calcination. The hydrogen form can also be prepared directly by exchange with an acid. The hydrogen-form and forms containing metals introduced by ion exchange are described further below.

We believe that zeolite EU-4 is, like zeolite EU-1, yet another member of the ZSM-23 family of zeolites (as described for example, in U.S. Pat. No. 4,076,842, although our attempts to make ZSM-23 in accordance with this and other published descriptions have so far been unsuccessful). An analogy can be drawn with the relationship between the aforesaid ZSM-23 family of zeolites and the ZSM-5/ZSM-11 family of zeolites (as described, for example in U.S. Pat. Nos. 3,702,886 and 3,709,979; and in Nature, 1978, 275, 119), which from the literature appear to have similar X-ray diffraction data, but in fact have related, but significantly different, three dimensional frameworks.

Zeolite EU-4 has molecular sieve properties analogous to those of known zeolites. Thus zeolite EU-4 may be characterised by its adsorption for molecules of vari-

TABLE I

| X-ray data on 'as made' EU-4 | | | | | | | | | | |
|---|---|---|---|---|---|---|---|---|---|---|
| dA | 11.1 ± 0.2 | 9.2 ± 0.2 | 4.62 ± 0.08 | 4.46 ± 0.08 | 4.28 ± 0.08 | 3.98 ± 0.08 | 3.69 ± 0.06 | 3.58 ± 0.06 | 3.34 ± 0.06 | 3.26 ± 0.05 |
| I | vs | w → vs | vs | w → s | vs | vs | s | s | s | s → vs |

TABLE 2

Comparison X-ray data of EU-4, EU-1 and ZSM23

| EU-4 | | EU-1 | | ZSM23 | |
|---|---|---|---|---|---|
| dA | I | dA | I | dA | I |
| 11.1 ± 0.2 | vs | 11.03 | vs | 11.2 ± 0.23 | m |
| — | — | 10.10 | s | 10.1 ± 0.2 | w |
| — | — | 9.72 | w | — | — |
| 9.2 ± 0.2 | w→vs | — | — | — | — |
| — | — | — | — | 7.87 ± 0.15 | w |
| 7.62 ± 0.15 | m | — | — | — | — |
| 6.87 ± 0.15 | m | 6.84 | w | — | — |
| 6.29 ± 0.1 | m | — | — | — | — |
| 5.98 ± 0.1 | w→m | 5.86 | vw | — | — |
| — | — | — | — | 5.59 ± .1 | w |
| — | — | — | — | 5.44 ± 0.1 | w |
| — | — | — | — | 4.9 ± 0.1 | w |
| 4.63 ± 0.08 | vs | 4.66 | vs | 4.53 ± 0.1 | s |
| 4.47 ± 0.08 | w→s | — | — | — | — |
| 4.29 ± 0.08 | vs | 4.31 | vs | — | — |
| 3.98 ± 0.08 | vs | 4.00 | vs | 3.90 ± 0.08 | vs |
| 3.80 ± 0.08 | w | 3.82 | s | — | — |
| 3.75 ± 0.06 | m | 3.71 | s | 3.72 ± 0.08 | vs |
| 3.68 ± 0.06 | s | — | — | 3.63 | vs |
| 3.58 ± 0.06 | w→s | — | — | 3.54 ± 0.07 | m |
| 3.42 ± 0.06 | m | 3.44 | m | 3.44 ± 0.07 | s |
| 3.32 ± 0.06 | s | 3.38 | m | 3.36 ± 0.07 | w |
| 3.27 ± 0.05 | s→vs | 3.26 | s | — | — |
| 3.23 ± 0.05 | m | — | — | — | — |
| 3.11 ± 0.05 | w | 3.16 | vw | 3.16 ± 0.07 | w |

The data for EU-1 are taken from published European Patent Application No. 42226A.
The data for ZSM-23 are taken from U.S. Pat. No. 4076842.

In Table 2 X-ray data for zeolites EU-4, EU-1 and ZSM 23 are compared. It can be seen that while there are similarities there are also very significant differences in relation to major d-spacings which clearly demonstrate very significant differences exist between the structures of the three zeolites.

Within the above definition of chemical composition, the number of moles of $Y_2O_3$ is in the range 0 to 9 and zeolite EU-4 appears to be most readily formed in a ous sizes. Typical results are shown in Table 3. These results show that EU-4 has hydrophobic characteristics because the voidage available to n-hexane is much greater than for water.

TABLE 3

| | Sorption at 25° C. on EU-4 (Example 1) calcined at 450° C. (70 hours) | | | | |
|---|---|---|---|---|---|
| Adsorbate | Kinetic* Diameter σA | Pressure mm Hg | Time Hours | Wt sorbed g/100 g | Voidage available cc/100 g |
| Water | 2.7 | 6.0 | 16 | 0.78 | 0.78 |
| n-Hexane | 4.3 | 49 | 17 | 1.96 | 2.97 |
| cyclohexane | 6.0 | 27.6 | 18.0 | 1.76 | 2.25 |

*Lennard Jones kinetic diameter see D W Breck "Zeolite Molecular Sieves", Wiley Interscience, 1974 p 636

The invention provides also a method of making zeolite EU-4 which comprises reacting an aqueous mixture comprising at least one oxide $XO_2$, and optionally at least one oxide $Y_2O_3$, and at least one alkylated trimethyl ammonium or dialkyl dimethyl ammonium compound, the mixture having the molar composition:

$XO_2/Y_2O_3$: at least 10, preferably at least 40
$OH^-/XO_2$: 0.1 to 6.0, preferably 0.1 to 1.0
$(M_1^+ + Q^+)/XO_2$: 0.05 to 2.0
$Q^+/(M_1^+ + Q^+)$: 0.1 to 1.0
$H_2O/XO_2$: 1 to 100
$M_2Z/H_2O$: $10^{-4}$ to 0.5, preferably $10^{-2}$ to 0.3 where X is silicon and/or germanium, Y is one or more of aluminium, iron, chromium, vanadium, molybdenum, arsenic, antimony, manganese, gallium or boron, $M_1$ and $M_2$ are alkali metal or ammonium or hydrogen, and Q is the aforesaid alkyl trimethyl compound $R_1(CH_3)_3N$ or dialkyl dimethyl compound $R_1R_2(CH_3)_2N$, an amine degradation product thereof, or a precursor thereof, or a related compound, and wherein $R_1$ and $R_2$, which may be the same or different, are alkyl groups containing from 2 to 10 carbon atoms, preferably 3 to 6 carbon atoms.

$M_1$, $M_2$ and/or Q can be present as hydroxides or salts of inorganic or organic acids provided the $OH^-/XO_2$ requirement is fulfilled. $M_2$ can be the same as or different from $M_1$. Z is a strong acid radical. Propyl trimethylammonium compounds are the preferred organic components.

Suitable precursors of the quaternary cations starting materials include the parent amines along with alcohols or alkyl halides which can be used as such or can be preheated together in the reaction vessel preferably in solution (e.g. in methyl ethyl ketone) prior to addition of the other reactants required for zeolite EU-4 synthesis.

The preferred alkali metal ($M_1$ or $M_2$) is sodium. The preferred oxide $XO_2$ is silica ($SiO_2$) and the preferred oxide $Y_2O_3$ is alumina ($Al_2O_3$).

The silica source can be any of those commonly considered for use in synthesising zeolites, for example powdered solid silica, silicic acid, colloidal silica or dissolved silica. Among the powdered silicas usable are precipitated silicas, especially those made by precipitation from an alkali metal silicate solution, such as the type known as "KS 300" made by AKZO, and similar products, aerosil silicas, fume silicas and silica gels suitably in grades for use in reinforcing pigments for rubber or silicone rubber. Colloidal silicas of various particle sizes may be used, for example 10-15 or 40-50 microns, as sold under the Registered Trade Marks "LUDOX", "NALCOAG" and "SYTON". The usable dissolved silicas include commercially available waterglass silicates containing 0.5 to 6.0, especially 2.0 to 4.0 mols of $SiO_2$ per mol of alkali metal oxide, "active" alkali metal silicates as defined in UK Pat. No. 1193254, and silicates made by dissolving silica in an alkali metal hydroxide or quaternary ammonium hydroxide or a mixture thereof.

The alumina source is most conveniently sodium aluminate, but aluminium, an aluminium salt, for example the chloride, nitrate or sulphate, an aluminium alkoxide or alumina itself, which should preferably be in a hydrated or hydratable form such as colloidal alumina, pseudoboehmite, boehmite, gamma alumina or the alpha or beta trihydrate.

The reaction mixture is usually reacted under autogenous pressure, optionally with added gas, e.g. nitrogen, at a temperature between 85° and 250° C. until crystals of zeolite EU-4 form, which can be from 1 hour to many months depending on the reactant composition and the operating temperature. Agitation is optional, but is preferable since it reduces the reaction time.

At the end of the reaction, the solid phase is collected on a filter and washed and is then ready for further steps such as drying, dehydration and ion-exchange.

If the product of the reaction contains alkali metal ions, these have to be at least partly removed in order to prepare the hydrogen form of EU-4 and this can be done by ion exchange with an acid, especially a strong mineral acid such as hydrochloric acid or by way of the ammonium compound, made by ion exchange with a solution of an ammonium salt such as ammonium chloride. Ion exchange can be carried out by slurrying once or several times with the ion-exchange solution. The zeolite is usually calcined after ion exchange but this may be effected before ion-exchange or during ion-exchange if the latter is carried out in a number of stages.

In general, the cation(s) of zeolite EU-4 can be replaced by any cation(s) of metals; and particularly those in Groups IA, IB, IIA, IIB, III (including rare earths) VIII (including noble metals) and by lead, tin, and bismuth. (The Periodic Table is as in "Abridgements of Specifications" published by the UK Patent Office). Exchange is carried out using any water soluble salts containing the appropriate cation.

When used as a catalyst, zeolite EU-4 can be associated with an inorganic matrix, which can be either inert or catalytically active. The matrix may be present simply as a binding agent to hold the small zeolite particles (0.005 to 10 microns) together, or it may be added as a diluent to control the amount of conversion in a process which may otherwise proceed at too high a rate, leading to catalyst fouling as a result of excessive coke formation. Typical inorganic diluents include catalyst support materials such as alumina, silica and kaolinic clays, bentonites, montmorillonites, sepiolite, attapulgite, Fullers earth, synthetic porous materials such as $SiO_2$-$Al_2O_3$, $SiO_2$-$ZrO_2$, $SiO_2$-$ThO_2$, $SiO_2$-$BeO$, $SiO_2$-$TiO_2$ or any combination of these diluents. An effective way of mixing zeolite EU-4 with such diluents is to mix appropriate aqueous slurries in a mixing nozzle and then to spray-dry the slurry. Other ways of mixing can be used.

If zeolite EU-4 in any cationic form or as a catalytic composite is exchanged or impregnated with hydrogenation/dehydrogenation components, such as Ni, Co, Pt, Pd, Re, Rh, hydrocracking and reforming catalysts can be made, especially if the $Na_2O$ content is less than 0.1% w/w.

A wide range of hydrocarbon conversion catalysts can be prepared from zeolite EU-4 by ion exchange or impregnation with cations, or oxides, selected from the following, Cu, Ag, Mg, Ca, Sr, Zn, Cd, B, Al, Sn, Pb, V, P, Sb, Cr, Mo, W, Mn, Re, Fe, Co, Ni, noble metals.

Usually the EU-4 catalyst will be in acid form, thus stoichiometry is maintained by $H^+$ or $H_3O^+$ as an additional balancing cation, or as sole cation. Such catalysts may find application in the following processes; catalytic cracking, hydrodesulphurization, hydrodenitrification, catalytic dewaxing, alkylation of alkanes or aromatics, dealkylation, disproportionation, isomerisation of alkanes and alkyl benzenes e.g. xylenes, dehydration reactions, oxidation, polymerisation and conversion of methanol to olefins. Zeolite EU-4 may also find applications in the separation of aromatics and cycloparaffins, and in pollution control by its ability to remove organic contaminants from aqueous effluents as a result of its hydrophobic nature.

tion mixture. The purpose of the addition was to increase the rate of formation of EU-4.

The products were washed with water equivalent to about twice the original volume of the reaction mixture, dried overnight at 100° C. and then equilibrated in moist air.

The product of Example 1 had the following composition:

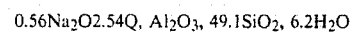
$0.56Na_2O 2.54Q, Al_2O_3, 49.1SiO_2, 6.2H_2O$ and X-ray diffraction data as shown in Table 5.

The product of Example 2 had the composition: $0.22Na_2O, 2.94Q, Al_2O_3, 55.1SiO_2, 8.2H_2O$ and X-ray diffraction data are as shown in Table 6.

The product of Example 4 had a $SiO_2/Al_2O_3$ about 5000 and the X-ray data as shown in Table 7.

The X-ray diffraction data for the product of Example 6 are shown in Table 8.

TABLE 4

Synthesis of EU-4

| Example | Composition of Reaction Mixture | | | | | Temp °C. | Time Hours | Product |
|---|---|---|---|---|---|---|---|---|
| | $Na_2O$ | Q | $Al_2O_3$ | $SiO_2$ | $H_2O$ | | | |
| 1 | 10 | 20 | 1 | 60 | 3000 | 180 | 90 | major EU-4 |
| 2 | 3 | 20 | 1 | 60 | 3000 | 180 | 170 | major EU-4 |
| 3 | 10 | 20 | 0.01 | 60 | 3000 | 200 | 17 | EU-4 + α quartz |
| 4 | 10 | 20 | 0.01 | 60 | 3000 | 180 | 19 | major EU-4 |
| 5 | 10 | 20 | 2 | 60 | 3000 | 180 | 268 | minor EU-4 |
| 6 | 10 | 20 | 2 | 60 | 3000 | 180 | 144 | major EU-4 |

TABLE 5

X-ray data on EU-4 (Example 1)

| dA | 11.07 | 9.22 | 7.52 | 6.83 | 6.28 | 5.97 | 5.83 | 4.594 | 4.450 | 4.292 | 3.967 | 3.768 | 3.688 |
|---|---|---|---|---|---|---|---|---|---|---|---|---|---|
| dA | 3.571 | 3.425 | 3.338 | 3.269 | 3.128 | 3.073 | 3.027 | 3.004 | 2.854 | 2.780 | 2.746 | 2.687 | 2.571 |

TABLE 6

X-ray data on EU-4 (Example 2)

| dA | 11.07 | 9.22 | 7.56 | 6.83 | 6.28 | 5.99 | 5.83 | 4.594 | 4.450 | 4.280 | 3.967 | 3.723 | 3.671 |
|---|---|---|---|---|---|---|---|---|---|---|---|---|---|
| dA | 3.563 | 3.417 | 3.338 | 3.263 | 3.223 | 3.116 | 3.079 | 3.021 | 2.993 | 2.839 | 2.780 | 2.742 | 2.678 |

TABLE 7

X-ray data on EU-4 (Example 4)

| dA | 11.03 | 9.20 | 7.62 | 6.87 | 6.29 | 5.98 | 4.628 | 4.469 | 4.286 | 3.982 | 3.799 | 3.754 | 3.675 |
|---|---|---|---|---|---|---|---|---|---|---|---|---|---|
| Intensity | vs | vs | m | m | m | m | vs | s | vs | vs | w | m | s |
| dA | 3.584 | 3.421 | 3.342 | 3.314 | 3.266 | 3.226 | 3.106 | 3.076 | 3.001 | 2.979 | 2.846 | 2.749 | 2.685 |
| Intensity | s | m | s | w | s | m | w | w | vw | vw | m | w | m |

The invention is illustrated by the following Examples.

EXAMPLES 1-6

The invention is illustrated by the examples given in Table 4, in which Q was propyltrimethylammonium bromide, and the silica source was CAB-O-SIL M5. In Examples 1, 2, 5 and 6 the alumina source was Nalfloc sodium aluminate (1.25 $Na_2O$, $Al_2O_3 2H_2O$). In Examples 3 and 4, the alumina was an impurity in the silica source and may even be present in the product as an aluminous impurity. In Example 6, a quantity of the dried, as synthesised material from Example 1 was added as seed material. The quantity added corresponded to approximately 5% (w/w) of the solid silica added. The term seed material, above, is used to describe the addition of some pre-formed EU-4 to a reac-

TABLE 8

X-ray data on EU-4 (Example 6)

| dA | 11.11 | 10.06 | 9.22 | 6.87 | 6.26 | 5.91 | 4.66 | 4.48 | 4.33 |
|---|---|---|---|---|---|---|---|---|---|
| Intensity | vs | w | w | m | vw | w | vs | w | vs |
| dA | 4.00 | 3.84 | 3.71 | 3.60 | 3.46 | 3.44 | 3.36 | 3.28 | 3.17 |
| Intensity | vs | vw | s | w | m | m | s | vs | vw |
| dA | 3.11 | 3.0 | 2.95 | 2.71 | 2.59 | 2.54 | | | |
| Intensity | w | m | vw | w | vw | w | | | |

EXAMPLE 7

A sample of the dried product from Example 6 was calcined in a stream of flowing air at 450° C. for 72 hours. The calcined material was then ion-exchanged with N/1 HCl, 50 cm³ acid per g zeolite, at 60° C. for 4 hours. After ion-exchange, the material was washed with deionised water and dried at 110° C. for several hours, then pelleted, broken down and sieved. A portion of the catalyst particle size 710–1000μ was charged to a through-flow reactor. The catalyst was activated at 450° C. under a flow of helium for 1 hour. Then a flow of methanol in helium (55% methanol) was passed over the catalyst, at 450° C., at a WHSV of 1.33 g methanol per g of catalyst per hour. Details of the products obtained after 84 minutes on stream can be seen below:

Time on stream: 84 minutes
Conversion of methanol: 100%
Methanol converted to $C_1$–$C_4$ hydrocarbons (Carbon basis): approx 60%

| Distribution of $C_1$–$C_4$ hydrocarbons (Carbon basis) % | |
| --- | --- |
| Methane | 2.6 |
| Ethane | 0.1 |
| Ethene | 4.6 |
| Propane | 3.5 |
| Propene | 43.3 |
| Butanes | 24.2 |
| Butenes | 21.7 |

What we claim is:

1. A synthetic zeolite material having a molar composition expressed by the formula:

0 to $9M_2O$:a$Y_2O_3$:at least 100 $XO_2$:0 to 35$H_2O$ wherein M is a monovalent cation or 1/n of a cation of valency n, a is from 0 to 9, X is silicon and/or germanium, Y is one or more of aluminium, iron, chromium, vanadium, molybdenum, arsenic, antimony, manganese, gallium or boron, and $H_2O$ is water of hydration additional to water notionally present when M is H, and having an X-ray pattern substantially as set out in Table 1.

2. A synthetic zeolite material according to claim 1 having a molar composition expressed by the formula:

0 to $9M_2O$:0 to 2.5$Y_2O_3$:at least 100 $XO_2$:0 to 35$H_2O$.

3. A synthetic zeolite material according to claim 1 or claim 2 wherein M is hydrogen resulting from the calcination of the material in the presence of air.

4. A method of making a synthetic zeolite as defined in claim 1 or claim 2 which comprises reacting an aqueous mixture comprising at least one oxide $XO_2$, optionally at least one oxide $Y_2O_3$ and a propyltrimethylammonium compound, the mixture having the molar composition:

$XO_2/Y_2O_3$: at least 10
$OH/XO_2$: 0.1 to 6.0
$(M_1+Q^+)/XO_2$: 0.05 to 2.0
$Q^+/(M_1^++Q^+)$: 0.1 to 1.0
$H_2O/XO_2$: 1 to 100
$M_2Z/H_2O$: $10^{-4}$ to 0.5 wherein X and Y have the meanings given in claim 1, $M_1$ and $M_2$ are alkali metal, ammonium or hydrogen, Q is a propyltrimethylammonium compound and Z is a strong acid radical.

5. A method according to claim 4 wherein $XO_2/Y_2O_3$ is at least 40.

6. A method according to claim 4 wherein $OH^-/XO_2$ is in the range 0.1 to 1.0.

7. A method according to claim 4 wherein $M_2Z/H_2O$ is in the range $10^{-2}$ to 0.3.

8. A catalyst comprising a synthetic zeolite material as claimed in claim 1 or claim 2.

* * * * *